US00PP15796P3

(12) United States Plant Patent
de Groot

(10) Patent No.: US PP15,796 P3
(45) Date of Patent: Jun. 14, 2005

(54) HYBRID TEA ROSE PLANT NAMED 'RUIZ99925'

(50) Latin Name: *Rosa hybrid*
Varietal Denomination: RUIZ99925

(75) Inventor: Henk C. A. de Groot, De Kwakel (NL)

(73) Assignee: De Ruiter's Nieuwe Rozen B.V., De Kwakel (NL)

( * ) Notice: Subject to any disclaimer, the term of this patent is extended or adjusted under 35 U.S.C. 154(b) by 0 days.

(21) Appl. No.: 10/615,633

(22) Filed: Jul. 8, 2003

(65) Prior Publication Data

US 2004/0123354 P1 Jun. 24, 2004

(30) Foreign Application Priority Data

Dec. 20, 2002 (EP) ..... 2002/2145
Jan. 27, 2003 (PL) ..... O1387/TO1473

(51) Int. Cl.[7] ..... A01H 5/00
(52) U.S. Cl. ..... Plt./134
(58) Field of Search ..... Plt./132, 134

(56) References Cited

U.S. PATENT DOCUMENTS

PP13,115 P2 * 10/2002 Winchel ..... Plt./132

OTHER PUBLICATIONS

UPOV ROM GTITM Computer Database 2004/02, GTI Jouve Retrieval Software Citation for 'RUIZ99925'.*

* cited by examiner

*Primary Examiner*—Kent Bell
*Assistant Examiner*—W C Haas
(74) *Attorney, Agent, or Firm*—Christie, Parker & Hale, LLP

(57) ABSTRACT

A new and distinct Hybrid Tea Rose plant having flowers with yellow cream central petals and greenish outer petals.

2 Drawing Sheets

Botanical classification: The present invention relates to a new Hybrid Tea Rose, *Rosa* hybrid.

Variety denomination: The new rose plant has the varietal name 'RUIZ99925'.

BACKGROUND OF THE INVENTION

The present invention relates to a new and distinct variety of rose plant of the Hybrid Tea rose class, which was created by crossing as seed parent and pollen parents unnamed, undistributed seedlings. The varietal denomination of this new rose is named 'RUIZ99925'.

SUMMARY OF THE INVENTION

Among the novel characteristics possessed by this new variety which distinguishes it from its parents and all other varieties of which I am aware are its unusual and attractive flowers exhibiting yellow cream central petals and greenish-hued outer petals.

Asexual reproduction by propagation by grafting and vegetative cutting of the new variety as performed in De Kwakel, The Netherlands shows that the foregoing and other distinguishing characteristics come true to form and are established and transmitted through succeeding propagation.

COMPARISON WITH PARENTS

Among other respects, the new variety differs from its parents in flower color. The seed parent and the pollen parent are unknown; the new variety was discovered as a single seedling in a controlled planting of mixed rose varieties.

BRIEF DESCRIPTION OF ILLUSTRATIONS

The accompanying illustration show a typical specimens of the new variety depicted in color as nearly true as is reasonably possible to make the same in a color illustration of this character.

Figure 1:
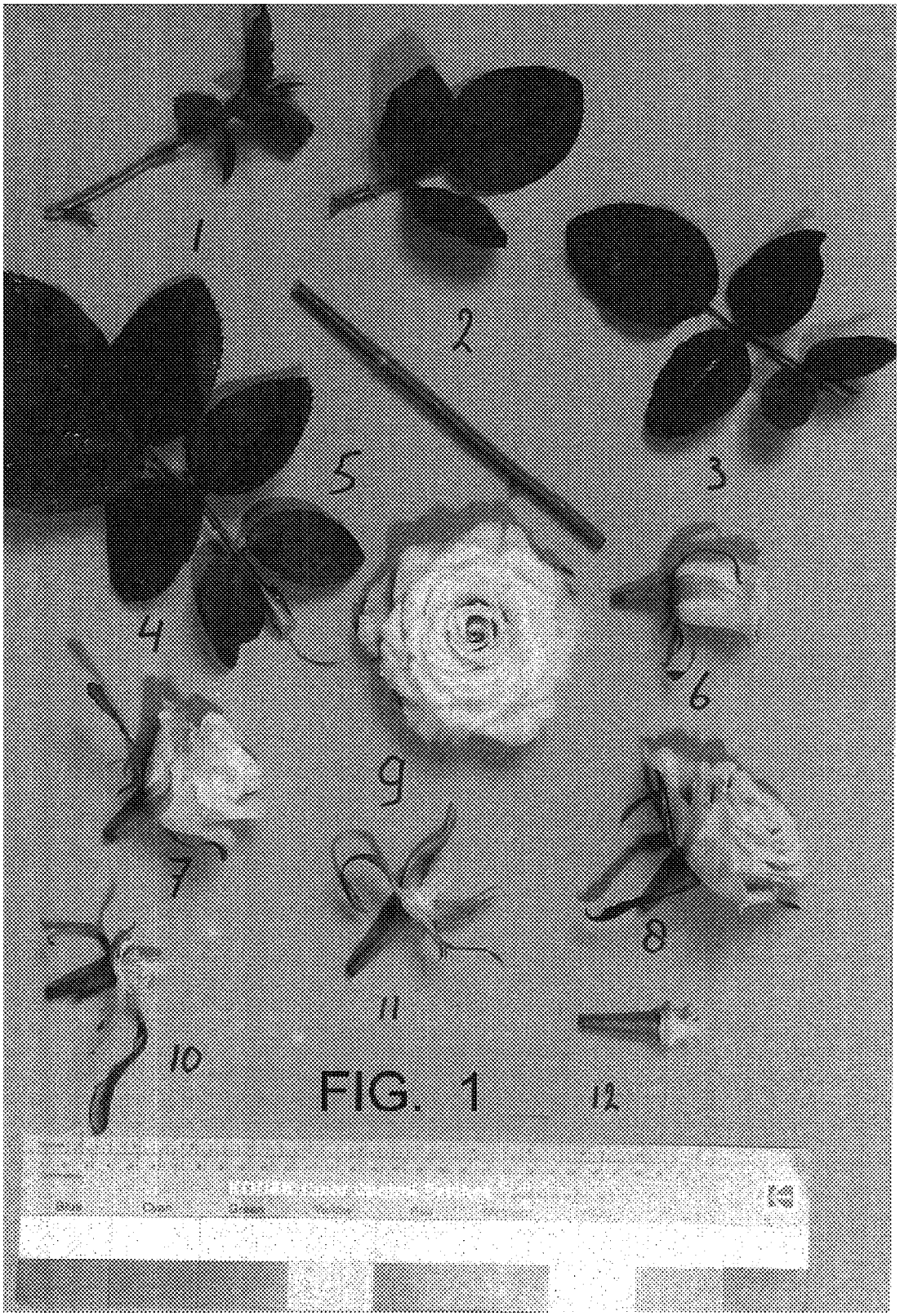

FIG. 1 shows: new growth 1; leaflets 2, 3, and 4; stem with thorns 5; flowers in different stages of development 6, 7, 8 and 9; and reproductive organs 10, 11 and 12.

Figure 2:
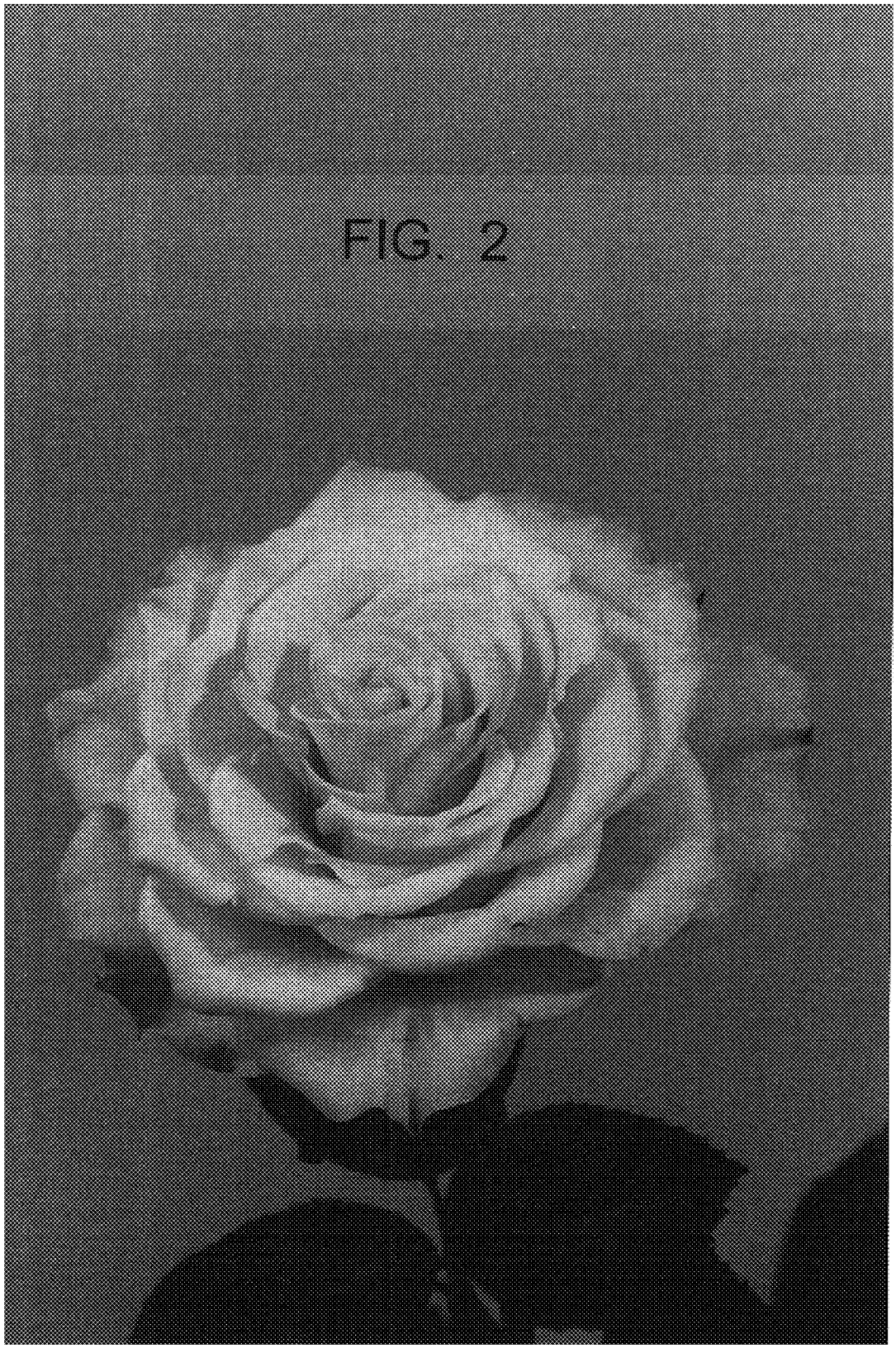

FIG. 2 shows a flower of the new variety about ⅓ to ½ open.

DESCRIPTION OF THE NEW VARIETY

The following is a detailed description of the new variety with color terminology in accordance with The Royal Horticultural Society Colour Chart (R.H.S.C.C.). The terminology used in color description herein refers to plate numbers in the aforementioned color chart. Phenotypic expression may vary with light availability, environmental and cultural conditions.

The following observations are made of 9-month old plants grown in a greenhouse in De Kwakel, The Netherlands during May from a grafted cutting. The plant was grown in a 12 liter pot with a coco peat substrate. Average day temperature was between 20 and 22 degrees Celsius. The plant was gown on its own roots.

FLOWER

Blooming habit: Continuous.

Bud:

*Size.*—About 5 cm long, about 4 cm wide.

*Form.*—Wide ovate.

Color:

*Outside.*—Near 3C at base to near 4D in middle, margin near 144D.

*Inner side.*—Base near 9C, middle near 19C, margin near 144D.

*Sepals.*—Just before opening sepals are as long as the bud, about 5 cm, about 1 cm wide at base, occasionally one of the sepals has a foliaceous end.
*Upper surface.*—Smooth, near 144A.
*Undersurface.*—Hairy, near 144A.
Peduncle:
*Length.*—About 12 cm.
*Diameter.*—About 6–8 mm.
*Aspect.*—Smooth with few prickles at the base.
*Strength.*—Strong, erect.
*Color.*—Near 144A.
Bloom:
*Size.*—Average size when fully open about 12 cm.
*Borne.*—Singly.
*Form.*—Shape viewed from above is irregularly round; upper part is flattened convex; lower part is flat,
*Petalage.*—About 35 petals.
Color (⅓ to ½ open):
Outer petals:
*Top surface.*—Near 150D, margin near 149B.
*Undersurface.*—Near 150D, margin near 145B.
Inner petals:
*Top surface.*—Near 19C.
*Undersurface.*—Near 11D.
Base of petals:
(*Point of attachment*).—Near 10C.
*General tonality from a distance.*—Light yellow-pink.
Color (fully open):
Outer petals:
*Top surface.*—Near 1D, margin near 144C.
*Undersurface.*—Near 1D, margin near 144C.
Inner petals:
*Top surface.*—Near 19B, margin near 27A.
*Undersurface.*—Near 10C.
Base of petals:
(*Point of attachment*).—Near 7A.
*General tonality from a distance.*—Orange-pink with green margin.
Color change:
*As bloom ages.*—The yellow bud develops into a green-colored flower with a pink inner surface.
*Petal top surface.*—Near 150D.
*Petal undersurface.*—Near 150D.
*General tonality at a distance.*—Cream-pink.
Petals:
*Length.*—About 5.3 to 5.7 cm.
*Width.*—About 5.0 to 5.5 cm.
*Texture.*—Inner side smooth, outside veined.
Appearance:
*Inside.*—Satiny.
*Outside.*—Satiny.
*Form.*—Elliptic.
*Arrangement.*—Imbricated.
*Petaloid.*—
*Color.*—Upper color, between 9C and 10B, sometimes lightly blushed between 27A and 27D.
*Texture.*—Thick.
*Size.*—Length approximately 1.5 cm to about 3.5 cm; width approximately 0.8 cm to 1.7.
*Petaloids in center.*—About 7.
*Persistence.*—Petals are persistent.
*Fragrance.*—Weak.
Lasting quality:
*Vase life.*—About 20 days.

REPRODUCTIVE ORGANS

Stamens, filaments and anthers:
*Arrangement.*—Irregularly around styles, about 50 stamens.
Color:
*Stamens.*—Near 7B.
*Filaments.*—Near 9C, about 5 mm long.
*Anthers.*—Near 13C.
*Pollen.*—Not abundant.
*Color.*—Near 199D.
*Styles.*—Uneven length 7 to 12 mm, near 8D.
Stigmas:
*Pistil.*—About 0.9 cm to about 1.4 cm in length, twisting and chary; color near 4D.
*Color.*—Near 22B.
*Hips.*—Seed production has not been observed.

PLANT

Form: Upright growing, long strong stems.
Growth: Vigorous, uniform branching.
Height attained (first season): About 200 cm.
Foliage: Average per stem from bottom to top: 2×5 leaflets, 3×7 leaflets, 2×5 leaflets, 3×3 leaflets.
Compound leaves: 5 leaflets about 17 cm in length, width about 13 cm.
Terminal leaflets: About 8 to 9.5 cm in length and about 5.5 to about 6.5 wide.
Size: About 10 cm long, width about 6 cm.
Quantity: About 10 leaflets per stem.
Color:
New foliage:
*Upper side.*—Shoot length about 30 cm, near 137C.
*Underside.*—Near 148B.
Mature foliage:
*Upper side.*—Stem length about 90 cm, near 139A.
*Underside.*—Near 138B.
*Shape.*—Elliptic.
Texture:
*Upper side.*—Glossy.
*Underside.*—Matte.
*Edge.*—Serrated.
*Serration* (*type*).—Serrate.
Petiole:
*Top surface.*—Near 138B.
*Underside.*—Near 145B.
*Stipules.*—Length about 22 mm, width about 9 mm; top surface smooth; color near 144B; undersurface smooth near 138B; shape — scale-like, margin serrate.
*Auricle.*—Length about 15 mm, width about 4 mm; margin, hairy, color near 138A.
Rachis:
*Length.*—Approximately 3 to about 5 mm.
*Diameter.*—Approximately 2 mm.
*Top surface.*—Smooth with raised border, color near 137C.
*Undersurface.*—Smooth and with a few prickles, color near 138C.
Resistance to disease:
*Blackspot.*—No natural resistance.
*Mildew.*—No natural resistance.
*Rust.*—No natural resistance.
Wood:
*Diameter of stems.*—About 7 to 9 mm, internode length about 6 to 8 cm.

*New shoots.*—Shoot length about 30 cm.
*Color.*—Near 138A.
*Bark.*—Smooth.

Old wood:
*Color.*—Near 139B.
*Bark.*—Smooth.
*Flower stem.*—About 90 to 100 cm.

Thorns:
*Number.*—Approximately 5 to 9 per stem.
*Form.*—Concave.
*Length.*—About 9 mm.
*Color* (*when young*).—Near 175A.
*Position.*—Irregular; scattered over the 6 lowest internodes.
*Prickles.*—Color near 181A.
*Winter hardiness.*—Not known, only grown in a glasshouse.

I claim:

1. A new and distinct Hybrid Tea Rose plant of the variety substantially as shown and described.

* * * * *